(12) United States Patent
Roessl et al.

(10) Patent No.: US 10,172,577 B2
(45) Date of Patent: Jan. 8, 2019

(54) X-RAY DETECTOR DEVICE FOR INCLINED ANGLE X-RAY RADIATION

(71) Applicant: KONINKLIJKE PHILIPS N.V., Eindhoven (NL)

(72) Inventors: Ewald Roessl, Ellerau (DE); Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/504,072

(22) PCT Filed: Dec. 1, 2015

(86) PCT No.: PCT/EP2015/078171
§ 371 (c)(1),
(2) Date: Feb. 15, 2017

(87) PCT Pub. No.: WO2016/087423
PCT Pub. Date: Jun. 9, 2016

(65) Prior Publication Data
US 2017/0285187 A1    Oct. 5, 2017

(30) Foreign Application Priority Data

Dec. 5, 2014  (EP) .................................... 14196550

(51) Int. Cl.
*G01T 1/24*         (2006.01)
*A61B 6/00*         (2006.01)
(Continued)

(52) U.S. Cl.
CPC .............. *A61B 6/4241* (2013.01); *A61B 6/42* (2013.01); *A61B 6/4208* (2013.01);
(Continued)

(58) Field of Classification Search
CPC ... A61B 6/4208; A61B 6/4233; A61B 6/4241; A61B 6/42; G01T 1/24; G01T 1/241
(Continued)

(56) References Cited

U.S. PATENT DOCUMENTS 5,111,052 A    5/1992  Ohtsuchi
5,677,539 A *  10/1997 Apotovsky ....... H01L 27/14676
                                                250/370.01
(Continued)

FOREIGN PATENT DOCUMENTS

JP    H02197178 A    8/1990
JP    2001274450 A   10/2001
(Continued)

*Primary Examiner* — Allen C. Ho
(74) *Attorney, Agent, or Firm* — Larry Liberchuk

(57) ABSTRACT

The invention relates to an X-ray detector device (10) for detection of X-ray radiation at an inclined angle relative to the X-ray radiation, an X-ray imaging system (1), an X-ray imaging method, and a computer program element for controlling such an X-ray imaging system for performing such method and a computer readable medium having stored such computer program element. The X-ray detector device (10) comprises a cathode surface (11) and an anode surface (12). The cathode surface (11) and the anode surface (12) are displaced by a separation layer (13) allowing charge transport (T) between the cathode surface (11) and the anode surface (12) in response to X-ray radiation incident during operation on the cathode surface (11). The anode surface (12) is segmented into anode pixels (121) and the cathode surface (11) is segmented into cathode pixels (111). At least one of the cathode pixels (111) is assigned to at least one of the anode pixels (121) in a coupling direction (C) inclined relative to the cathode surface (11). At least one of the cathode pixels (111) is configured to be at a voltage offset ΔU relative to an adjacent cathode pixel and at least one of the anode pixels (121) is configured to be at a voltage offset (Continued)

ΔU relative to an adjacent anode pixel (121). The voltage offset ΔU is configured to converge the charge transport (T) in a direction parallel to the coupling direction (C).

10 Claims, 3 Drawing Sheets

(51) Int. Cl.
  *H01L 31/0224*  (2006.01)
  *H01L 31/08*  (2006.01)
  *H01L 31/115*  (2006.01)
(52) U.S. Cl.
  CPC ............ *A61B 6/4233* (2013.01); *A61B 6/484* (2013.01); *G01T 1/24* (2013.01); *G01T 1/241* (2013.01); *H01L 31/0224* (2013.01); *H01L 31/085* (2013.01); *H01L 31/115* (2013.01)
(58) Field of Classification Search
  USPC .............................. 378/19, 98.8; 250/370.09
  See application file for complete search history.

(56) References Cited

U.S. PATENT DOCUMENTS

| | | | | |
|---|---|---|---|---|
| 5,701,011 A * | 12/1997 | Ohmori | ................ | G01T 1/2928 250/370.09 |
| 5,821,539 A * | 10/1998 | Matz | ................ | H01L 31/115 250/370.01 |
| 5,905,264 A * | 5/1999 | Shahar | .............. | H01L 27/14601 250/370.01 |
| 6,002,134 A * | 12/1999 | Lingren | ............ | H01L 27/14659 250/370.01 |
| 6,028,313 A * | 2/2000 | McDaniel | ............ | G01T 1/1642 250/338.4 |
| 6,034,373 A * | 3/2000 | Shahar | .............. | H01L 27/14676 250/338.4 |
| 6,037,595 A * | 3/2000 | Lingren | ................ | G01T 1/241 250/370.01 |
| 6,169,287 B1 * | 1/2001 | Warburton | ............ | G01T 1/2928 250/370.09 |
| 6,285,029 B1 * | 9/2001 | Shahar | ................ | G01T 1/202 250/370.1 |
| 6,333,504 B1 | 12/2001 | Lingren | | |
| 6,765,213 B2 * | 7/2004 | Shahar | ................ | G01T 1/2928 250/370.01 |
| 6,928,144 B2 * | 8/2005 | Li | ........................ | A61B 6/032 250/370.09 |
| 6,946,660 B2 * | 9/2005 | El-Hanany | .............. | G01T 1/241 250/370.13 |
| 6,953,935 B1 * | 10/2005 | Hoffman | ................ | G01T 1/242 250/370.13 |
| 7,092,481 B2 * | 8/2006 | Hoffman | .............. | A61B 6/4241 250/370.09 |
| 7,145,986 B2 * | 12/2006 | Wear | ........................ | G01T 1/366 250/370.09 |
| 7,196,332 B2 * | 3/2007 | Wear | ........................ | G01T 1/366 250/370.01 |
| 7,212,604 B2 * | 5/2007 | Tkaczyk | .............. | G01T 1/2985 378/19 |
| 7,223,982 B1 * | 5/2007 | Chen | .................... | G01T 1/2928 250/370.01 |
| 7,256,402 B1 * | 8/2007 | Lee | ........................ | G01T 1/241 250/370.09 |
| 7,260,174 B2 * | 8/2007 | Hoffman | ................ | A61B 6/032 250/363.09 |
| 7,391,845 B2 * | 6/2008 | Konno | ................ | A61B 6/032 250/208.1 |
| 7,560,700 B2 * | 7/2009 | Imai | ........................ | G01T 1/24 250/370.08 |
| 7,573,040 B2 * | 8/2009 | Tkaczyk | ................ | G01T 1/249 250/370.09 |
| 7,590,221 B2 * | 9/2009 | Durack | ................ | A61B 6/4283 378/162 |
| 7,606,347 B2 * | 10/2009 | Tkaczyk | ................ | A61B 6/032 378/19 |
| 7,613,274 B2 * | 11/2009 | Tkaczyk | ................ | A61B 6/032 378/19 |
| 7,634,061 B1 * | 12/2009 | Tümer | .................... | G01T 1/247 378/62 |
| 7,643,615 B2 * | 1/2010 | Wang | .................... | G03B 42/02 378/162 |
| 7,652,258 B2 * | 1/2010 | Shahar | ................ | G01T 1/24 250/370.01 |
| 7,728,301 B2 * | 6/2010 | Atsuta | .................... | G01T 1/249 250/370.09 |
| 7,916,831 B2 * | 3/2011 | Sun | ........................ | A61B 6/032 250/370.09 |
| 8,067,744 B2 * | 11/2011 | Blevis | .................... | G01T 1/241 250/370.01 |
| 8,165,266 B2 * | 4/2012 | Wear | ........................ | A61B 6/4042 250/370.13 |
| 8,212,327 B2 * | 7/2012 | Kurfiss | ............. | H01L 27/14603 257/104 |
| 8,314,395 B2 * | 11/2012 | Zhang | .................... | H01L 31/115 250/370.08 |
| 8,405,038 B2 * | 3/2013 | Bouhnik | .................. | G01T 1/249 250/370.14 |
| 8,415,662 B2 * | 4/2013 | Ogusu | ................ | H01L 27/1462 257/42 |
| 8,426,826 B2 * | 4/2013 | Proksa | .................. | G01T 1/2928 250/370.09 |
| 8,610,081 B2 * | 12/2013 | Rao | ........................ | G01T 1/247 250/394 |
| 8,824,635 B2 * | 9/2014 | Tkaczyk | ................ | G01T 1/247 250/363.08 |
| 8,927,937 B2 * | 1/2015 | Schwarzman | .......... | G01T 1/244 250/370.01 |
| 9,000,389 B2 * | 4/2015 | Rusian | .................. | H01L 31/085 250/370.01 |
| 9,006,010 B2 * | 4/2015 | Shahar | .................. | H01L 31/085 257/623 |
| 9,018,589 B2 * | 4/2015 | Engel | ........................ | G01T 1/24 250/370.01 |
| 9,031,197 B2 * | 5/2015 | Spahn | ...................... | H04N 5/32 378/98.8 |
| 9,052,402 B2 * | 6/2015 | Dierre | .................... | G01T 1/241 |
| 9,069,088 B2 * | 6/2015 | Engel | .................... | G01T 1/241 |
| 9,097,810 B2 * | 8/2015 | Hackenschmied | ....... | G01T 1/24 |
| 9,113,542 B2 * | 8/2015 | Hackenschmied | ...... | H05G 1/30 |
| 9,202,961 B2 * | 12/2015 | Chen | .................... | H01L 31/085 |
| 9,207,332 B2 * | 12/2015 | Spahn | .................... | G01T 1/17 |
| 9,219,178 B2 * | 12/2015 | Zhang | ................ | H01L 31/02327 |
| 9,261,609 B2 * | 2/2016 | Shahar | .................... | G01T 1/241 |
| 9,297,912 B2 | 3/2016 | Campbell | | |
| 9,301,378 B2 * | 3/2016 | Steadman Booker | .... | G01T 1/24 |
| 9,408,585 B2 * | 8/2016 | Oh | ........................ | A61B 6/482 |
| 9,416,022 B2 * | 8/2016 | Saito | ...................... | C01G 29/00 |
| 9,423,515 B2 * | 8/2016 | Roessl | .................... | G01T 1/241 |
| 9,429,664 B2 * | 8/2016 | Crocco | ............ | H01L 27/14676 |
| 9,504,438 B2 * | 11/2016 | Proksa | .................... | G01T 1/24 |
| 9,504,439 B2 * | 11/2016 | Yi | ........................ | A61B 6/5205 |
| 9,517,045 B2 * | 12/2016 | Kang | .................... | G01N 23/087 |
| 9,535,171 B2 * | 1/2017 | Herrmann | ................ | G01T 1/241 |
| 9,603,577 B2 * | 3/2017 | Oh | ........................ | A61B 6/484 |
| 9,613,992 B2 * | 4/2017 | Shahar | ................ | H01L 27/1446 |
| 9,668,706 B2 * | 6/2017 | Kim | ........................ | A61B 6/563 |
| 9,675,309 B2 * | 6/2017 | Kim | ........................ | A61B 6/4266 |
| 9,700,269 B2 * | 7/2017 | Rodrigues | ............ | A61B 6/4241 |
| 9,750,467 B2 * | 9/2017 | Ergler | .................. | A61B 6/4233 |
| 9,753,156 B2 * | 9/2017 | Verbakel | ................ | G01T 1/24 |
| 9,759,822 B2 * | 9/2017 | Daerr | .................... | G01T 1/17 |
| 9,835,738 B2 * | 12/2017 | Göderer | ................ | G01T 1/247 |

(56) References Cited

U.S. PATENT DOCUMENTS

| 2013/0161523 | A1* | 6/2013 | Tkaczyk | G01T 1/241 |
| | | | | 250/370.13 |
| 2014/0319363 | A1* | 10/2014 | Engel | G01T 1/241 |
| | | | | 250/370.01 |

FOREIGN PATENT DOCUMENTS

| WO | 200054072 | A1 | 9/2000 |
| WO | 2010015959 | A2 | 2/2010 |
| WO | 2013012809 | A1 | 1/2013 |
| WO | 2013088352 | A2 | 6/2013 |

* cited by examiner

X-RAY DETECTOR DEVICE FOR INCLINED ANGLE X-RAY RADIATION

CROSS-REFERENCE TO PRIOR APPLICATIONS

This application is the U.S. National Phase application under 35 U.S.C. § 371 of International Application No. PCT/EP2015/078171, filed on Dec. 1, 2015, which claims the benefit of European Patent Application No. 14196550.9, filed on Dec. 5, 2014. These applications are hereby incorporated by reference herein.

FIELD OF THE INVENTION

The invention relates to an X-ray detector device for detection of X-ray radiation at an inclined angle, an X-ray imaging system, an X-ray imaging method, and a computer program element for controlling such device or system for performing such method and a computer readable medium having stored such computer program element.

BACKGROUND OF THE INVENTION

WO 2010/015959 (A2) discloses an X-ray photon detector for an imaging device comprising a cathode, a converter material and a substrate. The cathode comprises an outwardly extending plate and a base plate. The converter material is attached to a side of the outwardly extending plate. The substrate comprises an anode and is attached to the converter material.

WO 2013/088352 A2 discloses a radiation detector having an anode and a cathode segmented into anode and cathode segments, respectively. Herein the anode segments are provided with mutually different electrical potentials. A similar approach is adopted for the cathode segments.

U.S. Pat. No. 5,111,052 discloses a radiation sensor having a semiconductor substrate provide with a common electrode and a split electrode disposed on one and same surface of said substrate.

X-ray detection for X-ray imaging can be made with such semi-conductor X-ray detector arranged perpendicular or non-perpendicular inclined to the X-ray radiation. The inclined or edge-on detection has several benefits over perpendicular or face-on detection, among them an improved detective quantum efficiency for materials with lower atomic numbers, as e.g. silicon.

However, in case of an inclined detection and in particular when using lower atomic number detector materials, X-ray radiation entering into the X-ray detector is potentially shared over several detector electrodes leading to a spatial image resolution loss.

In detail, in case of an inclined detection, a direction of an electric field between a detector cathode and a detector anode makes an angle with respect to the direction of the incoming X-ray radiation, which is equal to an inclination angle of the incoming X-ray radiation with respect to the surface normal of the X-ray detector. A charge transported between the detector cathode and the detector anode can then be collected by either one of e.g. two adjacent detector anodes. Hence, the charge may be wrongly allocated with respect to a lateral position of an actual interaction site, which may lead to a degrading lateral image resolution and therefore to a spatial image resolution loss.

SUMMARY OF THE INVENTION

Hence, there may be a need to provide an improved X-ray detector device for detection of X-ray radiation at an inclined angle relative to the X-ray radiation, which allows a reduced spatial image resolution loss in inclined-angle irradiation X-ray detection.

The problem of the present invention is solved by the subject-matters of the independent claims, wherein further embodiments are incorporated in the dependent claims. It should be noted that the aspects of the invention described in the following apply also to the X-ray detector device, the X-ray imaging system, the X-ray imaging method, the computer program element, and the computer readable medium.

According to the present invention, an X-ray imaging detector is presented. The X-ray detector device comprises a cathode surface and an anode surface. The cathode surface and the anode surface are displaced by a separation layer allowing charge transport between the cathode surface and the anode surface in response to X-ray radiation incident during operation on the cathode surface.

The anode surface is segmented into anode pixels and the cathode surface is segmented into cathode pixels. At least one of the cathode pixels is assigned to at least one of the anode pixels in a coupling direction inclined relative to the cathode surface.

At least one of the cathode pixels is configured to be at a voltage offset relative to an adjacent cathode pixel and at least one of the anode pixels is configured to be at a voltage offset relative to an adjacent anode pixel. The voltage offset is configured to converge the charge transport in a direction parallel to the coupling direction. The voltage offset depends on an inclination angle between the cathode surface and the coupling direction, and the coupling direction is parallel to an axis of symmetry of a beam of X-ray radiation incident during operation on the cathode surface.

The coupling direction can be understood as parallel to an axis of symmetry of a beam of X-ray radiation incident during operation on the cathode surface. In case no fan- or cone-shaped beam of X-ray radiation is used, the coupling direction can be more easily understood as a direction parallel to the X-ray radiation radiating the cathode surface.

Herein "converging the charge transport parallel to the coupling direction C" implies that the direction of the charge transport T approaches the coupling direction C. Herein "approaching" allows for minor deviations between said directions. Such minor deviations for example may be due to variations in the electrical field that drive the charge transport and/or due to variations in the beam of X-ray radiation. The feasible amount of such minor deviations is determined by the desired spatial resolution of the X-ray image to be made. Herein "approaching" may also include an alignment or re-alignment of the charge transport direction and the coupling direction.

This converging of the charge transport parallel to the coupling direction is achieved by a voltage offset between adjacent cathode and anode pixels. The cathode and anode surfaces are pixilated and provided with a staggered high-voltage design to bring the charge transport direction in parallel with the coupling direction.

In detail, as the charge transport is hereby converged back in a direction parallel to the coupling direction, X-ray radiation entering into the X-ray detector is not anymore or to a lesser extent smeared over several cathode pixels 111 and/or anode pixels 121. Hence, a charge may not anymore or to a lesser extent be wrongly allocated with respect to a lateral position of an actual interaction site, which avoids or reduces a degrading lateral image resolution. As a result, the X-ray detector device according to the present invention improves spatial image resolution in inclined-angle irradiation X-ray detection. In other words, the inventions allows by simple means to restore the spatial image resolution to nominal values.

In an example, the inclination angle between the cathode surface and the coupling direction is between 5° and 89°, preferably between 10° and 60°, and more preferably between 15° and 50°. In other words, "inclined" excludes perpendicular and parallel.

In an example, the voltage offset is inversely proportional to an offset number x of cathode pixels between an arbitrary first cathode pixel and a second cathode pixel. The second cathode pixel is defined to be on an equipotential line with an anode pixel aligned with the first cathode pixel in a direction normal to the cathode surface. Exemplarily in other words, the offset number x is a pixel offset or a number of pixels used to align a predefined cathode pixel with an anode pixel parallel to the coupling direction which may be, simply put, the direction of incoming X-rays. This will be explained further below.

The same can be stated based on the anode pixels. Therefore, in an example, the voltage offset is inversely proportional to an offset number x of anode pixels between an arbitrary first anode pixel and a second anode pixel. The second anode pixel is defined to be on an equipotential line with a cathode pixel aligned with the first anode pixel in a direction normal to the cathode surface.

In an example, the voltage offset $\Delta U$ is $$\Delta U = \frac{U_C - U_A}{x}$$

or, in other words, the offset number x is $$x = \frac{U_C - U_A}{\Delta U}.$$

$U_C$ is a cathode voltage of a cathode pixel and $U_A$ is an anode voltage of an anode pixel. This anode pixel and this cathode pixel are aligned in a direction normal to the cathode surface. In other words, $U_C$ and $U_A$ are voltages on geometrically opposed anode and cathode pixels.

As an example, an estimate of a value of the voltage offset $\Delta U$ compared to a nominal high voltage setting $U_C$–$U_A$ can be obtained as follows: Assuming charge transport lines extend in a first direction, e.g. vertical, then lines of equal potential will be perpendicular to the first direction, here e.g. horizontal. Thus, a horizontal equipotential line starting at a specific anode pixel with a potential $U_A$ will end at a first cathode pixel which is offset by e.g. three pixels with respect to a second cathode pixel geometrically opposite (normal to the cathode surface) to the anode pixel with the potential $U_A$.

In an example, the offset number x is between 1 and infinity. The offset number x is preferably between 2 and 10. The offset number needs not to be an integer number.

In another example, the voltage offset $\Delta U$ is $$\Delta U = (U_C - U_A)\frac{p}{d}\tan\varphi.$$

Herein $U_C$ is again a cathode voltage of a cathode pixel and $U_A$ is an anode voltage of an anode pixel. This anode pixel and this cathode pixel are aligned in a direction normal to the cathode surface. In other words, $U_C$ and $U_A$ are voltages on geometrically opposed cathode pixels 111 and anode pixels 121. Further, p is an anode pitch, which means the distance between two adjacent anode pixels. Adjacent cathode pixels may have the same distance and pitch.

Moreover, d is the distance between the cathode surface and the anode surface.

$\varphi$ is the angle between the coupling direction and a cathode surface normal.

The ratio between pitch and distance p/d may be between 0.5 and 7, preferably between 0.5 and 5, and more preferably between 0.7 and 4.

According to the present invention, also an X-ray imaging system is presented. The X-ray imaging system comprises an X-ray detector device as described above and an X-ray tube configured to generate the beam of X-ray radiation incident during operation on the cathode surface of the X-ray detector device with an inclined angle between the axis of symmetry of the beam of X-ray radiation and the cathode surface. In an example, the X-ray imaging system further comprises a processing unit configured to process interference fringes detected by the X-ray detector device for phase-contrast imaging.

According to the present invention, also an X-ray imaging method is presented. It comprises the following steps, not necessarily in this order:
  providing X-rays to radiate a cathode surface of the X-ray detector device with an inclined angle, and
  detecting the X-rays by an X-ray detector device as described above.

In an example, the semiconductor X-ray detector device is illuminated at an angle to a detector surface normal such that a direction of drifting electrons and holes in the X-ray detector is on average different from a coupling direction, which is a direction of incoming X-rays or more precise, a direction parallel to an axis of symmetry of a beam of X-ray radiation.

In an example, adjacent cathode pixels and adjacent anode pixels are put at a constant high voltage offset with respect to one another in order to avoid a charge being carried away in a direction perpendicular to the cathode or anode surface. Such a voltage offset can be tuned to have a suitable polarity to converge a charge transport direction to the coupling direction. By converging the charge transport parallel to the coupling direction, an approach of the charge transport direction to the coupling direction is to be understood. Once implemented, charge can travel parallel to the coupling direction onto the anode pixels and a degradation of lateral spectral resolution is reduced or avoided.

In an example, the X-ray imaging method comprises the further steps of:
  measuring a resolution phantom for various values of the voltage offset, and calibrating the X-ray detector device by maximizing a spatial resolution as a function of the voltage offset.

The resolution phantom may be a line-pair that gives strong contrast to be used to assess resolution. The calibration can be made by a modulation transfer function (MTF) calibration method. The calibration can be made to maximize spatial resolution as a function of the voltage offset to achieve the best restoration. The calibration can be made to avoid imperfections in the high-voltage or resistances, which might lead to a mismatch between the coupling direction and the direction of charge transport.

This device, system or method can be used in slit-scanning mammography, as well as in detection concepts for Si-based CT detectors and phase-contrast tomo-synthesis.

According to the present invention, also a computer program element is presented, wherein the computer program element comprises program code means for causing an X-ray detector device as defined in the independent device claim to carry out the steps of the X-ray imaging method when the computer program is run on a computer controlling the X-ray detector device.

It shall be understood that the X-ray detector device, the X-ray imaging system, the X-ray imaging method, the computer program element for controlling such device and the computer readable medium having stored such computer program element according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
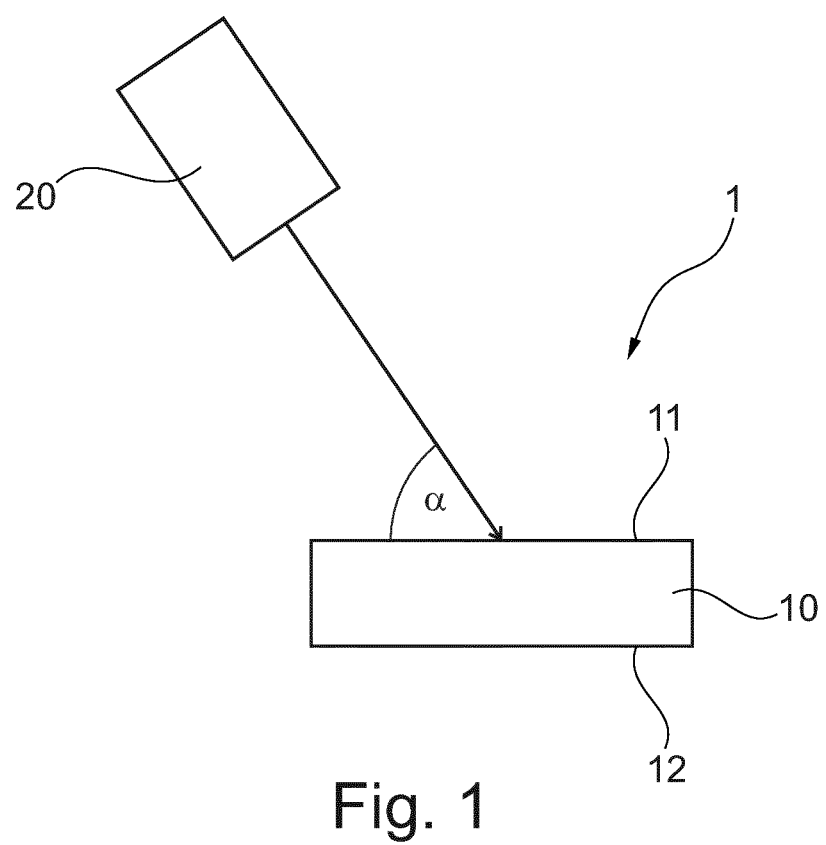
FIG. 1 shows a schematic drawing of an example of an X-ray imaging system according to the invention.

FIG. 1 shows schematically and exemplarily an embodiment of an X-ray imaging system 1 according to the invention. The X-ray imaging system 1 comprises an X-ray detector device 10 and an X-ray tube 20. The X-ray detector device 10 comprises a cathode surface 11 and an anode surface 12. The X-ray tube 20 during operation generates a beam of X-ray radiation radiating the cathode surface 11 of the X-ray detector device 10. The X-ray tube 20 is geometrically arranged above the X-ray detector device 10 such that an axis of symmetry of the X-ray beam is arranged at an inclination angle α relative to the cathode surface 11 of the X-ray detector device 10. Thereby, the X-ray beam generated by the X-ray tube 20 as shown in FIG. 1 by an arrow radiate the cathode surface 11 of the X-ray detector device 10 with an inclination angle α, which implies an angle being non-zero and being non-perpendicular.

Figure 2:
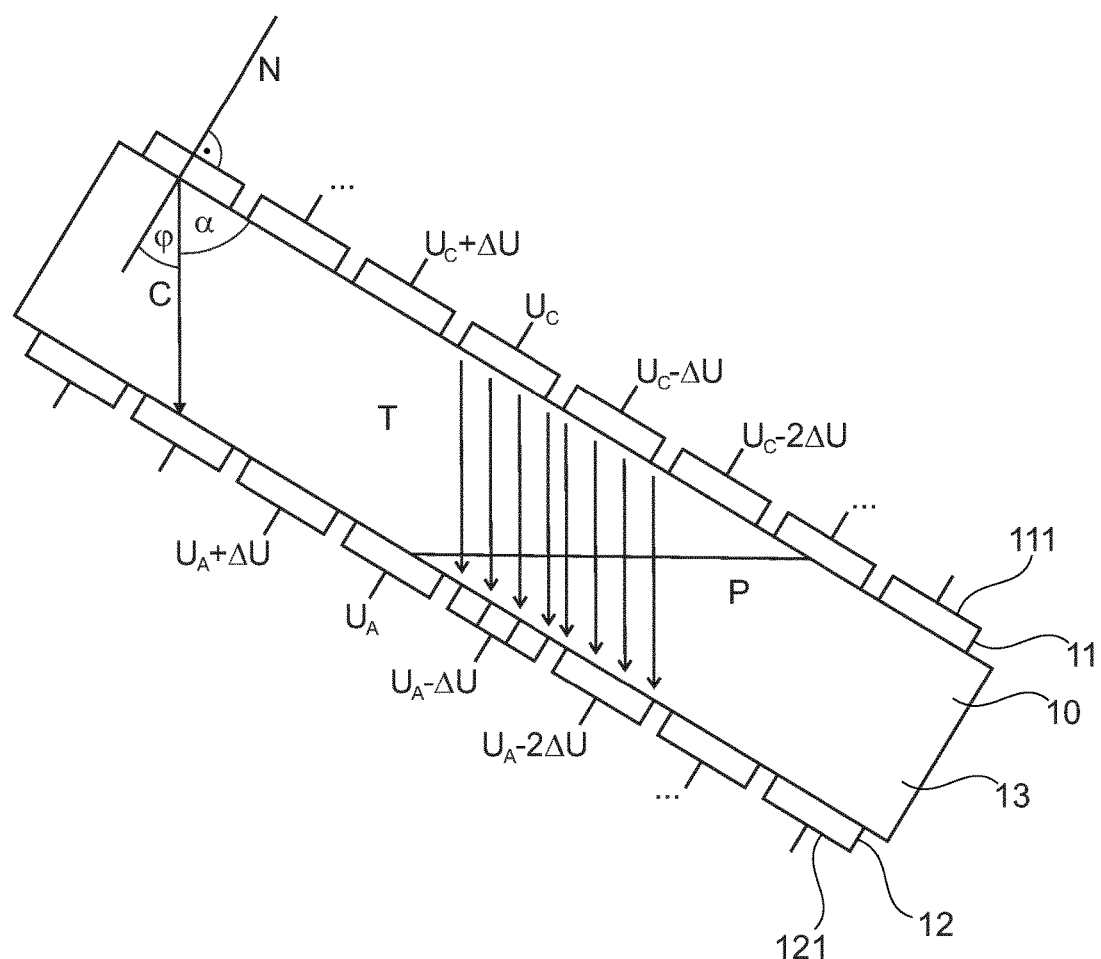
FIG. 2 shows schematically and exemplarily an embodiment of an X-ray detector device according to the invention.

FIG. 2 shows schematically and exemplarily an embodiment of an X-ray detector device 10 according to the invention. The X-ray detector device 10 is here e.g. a Di-Co-sensor comprising a cathode surface 11 and an anode surface 12. Between the cathode surface 11 and the anode surface 12, a separation layer 13 is arranged to allow a charge transport between the cathode surface 11 and the anode surface 12 in response to X-ray radiation incident during operation on the cathode surface 11. The direction of the charge transport T from the cathode surface 11 to the anode surface 12 is marked by arrows T.

The anode surface 12 is segmented into anode pixels 121 and the cathode surface 11 is segmented into cathode pixels 111. The cathode pixels 111 are assigned to the anode pixels 121 in a coupling direction C inclined relative to a cathode surface normal N by an angle φ. The coupling direction C can be understood as parallel to an axis of symmetry of a beam of X-ray radiation incident during operation on the cathode surface 11. The beam of X-ray radiation is shown in FIG. 2 as grey band. In case no fan- or cone-shaped beam of X-ray radiation is used, in which case the axis of symmetry of the X-ray beam is parallel to all X-rays comprised in the X-ray beam, the coupling direction C can more easily be understood as a direction parallel to the X-ray radiation radiating the cathode surface 11.

The cathode pixels 111 are at a voltage offset relative to the adjacent cathode pixels 111 and the anode pixels 121 are at a voltage offset relative to the adjacent anode pixels 121. The voltage offset is designed to converge the charge transport T between the cathode surface 11 and the anode surface 12 in a direction parallel to the coupling direction C. Herein "converging the charge transport T parallel to the coupling direction C" implies that the direction of the charge transport T approaches the coupling direction C. Herein "approaching" allows for minor deviations between said directions. Such minor deviations may for example be due to variations in the electrical field that drive the charge transport T and/or due to variations in the beam of X-ray radiation. The feasible amount of such minor deviations is determined by the desired spatial resolution of the X-ray image to be made.

Due to the voltage offset, the charge transport T is converged in a direction parallel to the coupling direction C. Thereby, the disadvantages of inclined detection compared to perpendicular detection can be overcome. That is: X-ray radiation entering into the X-ray detector device 10 is not anymore, or to a lesser extent, smeared over several cathode pixels 111 and/or anode pixels 121. Hence, a charge will not anymore, or at least to a lesser extent, be wrongly allocated with respect to a lateral position of an actual interaction site, which avoids or reduces a degrading lateral image resolution. As a result, a spatial image resolution in inclined-angle irradiation X-ray detection is improved.

The voltage offset ΔU depends on the inclination angle α between the cathode surface 11 and the coupling direction C. The inclination angle α between the cathode surface 11 and the coupling direction C amounts here to about 60°.

The voltage offset ΔU is inversely proportional to an offset number x of cathode pixels 111 between an arbitrary first cathode pixel and a second cathode pixel. The second cathode pixel is defined to be on an equipotential line P with an anode pixel aligned with the first cathode pixel in a direction N normal to the cathode surface 11. Exemplarily in other words, the offset number x is a pixel offset or a number of pixels used to align a predefined cathode pixel with an anode pixel parallel to the coupling direction C which may be, simply put, the direction of incoming X-rays. This will be explained based on the following example.

As an example, the voltage offset ΔU is $$\Delta U = \frac{U_C - U_A}{x}$$

or, in other words, the offset number x is $$x = \frac{U_C - U_A}{\Delta U}.$$

$U_C$ is a cathode voltage of a cathode pixel and $U_A$ is an anode voltage of an anode pixel. This anode pixel and this cathode pixel are aligned in a direction N normal to the cathode surface 11. In other words, $U_C$ and $U_A$ are voltages on geometrically opposed anode and cathode pixels.

An estimate of a value of the voltage offset $\Delta U$ compared to a nominal high voltage setting $U_C$–$U_A$ can be obtained as follows: Here, the charge transport lines T are designed to extend in a vertical direction. Then, equal potential lines P are perpendicular to the vertical charge transport lines T, which means horizontal. Thus, a horizontal equipotential line P starting at a specific anode pixel with a potential $U_A$ will end at a first cathode pixel which is offset by here three pixels with respect to a second cathode pixel geometrically opposite (normal to the cathode surface 11) to the anode pixel with the potential $U_A$. As a result, the offset number x in FIG. 2 is 3.

More generally, the voltage offset is $$\Delta U = (U_C - U_A)\frac{p}{d}\tan\varphi.$$

Herein $U_C$ is again a cathode voltage of a cathode pixel and $U_A$ is an anode voltage of an anode pixel geometrically opposing the cathode pixel. This anode pixel and this cathode pixel are aligned in a direction N normal to the cathode surface 11. In other words, $U_C$ and $U_A$ are voltages on geometrically opposed cathode pixels 111 and anode pixels 121. Furthermore, p is an anode pitch, which means the distance between two adjacent anode pixels 121. Adjacent cathode pixels 111 may have the same distance and pitch. Further d is the distance between the cathode surface 11 and the anode surface 12; and $\varphi$ is the angle between the coupling direction C and a cathode surface normal N.

The ratio p/d may be between 0.5 and 7, preferably between 0.5 and 5, and more preferably between 0.7 and 4.

Figure 3:
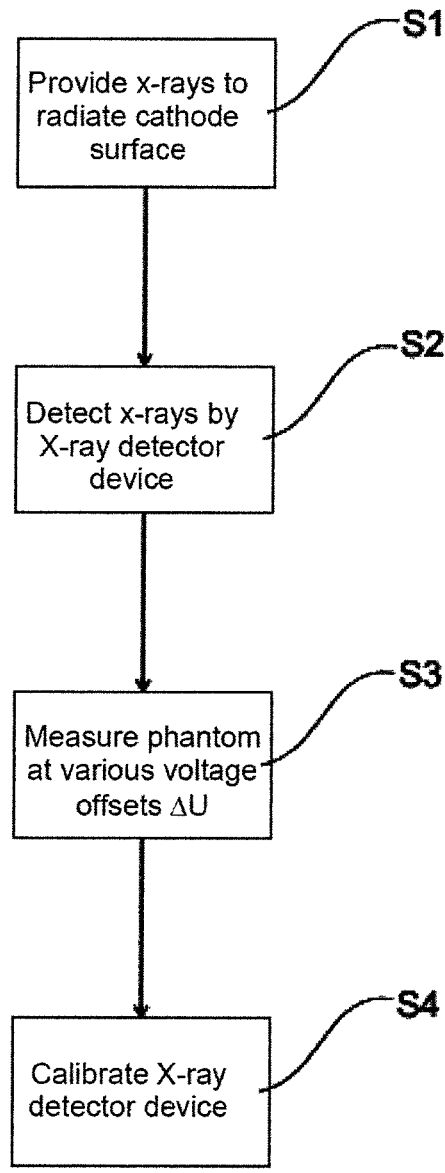
FIG. 3 shows a schematic overview of steps of an X-ray imaging method according to the invention.

FIG. 3 shows a schematic overview of steps of an X-ray imaging method according to the invention. The method comprises the following steps, not necessarily in this order:

In a first step S1, providing X-rays to radiate a cathode surface 11 of an X-ray detector device 10 with an inclination angle $\alpha$.

In a second step S2, detecting the X-rays by the X-ray detector device 10 as described above.

In an optional third step S3, measuring a resolution phantom for various values of the voltage offset $\Delta U$.

In an optional fourth step S4, calibrating the X-ray detector device 10 by maximizing a spatial resolution as a function of the voltage offset $\Delta U$.

In other words, the semiconductor X-ray detector device 10 is illuminated at an inclination angle $\alpha$ to a cathode surface 11 and an angle co to a cathode surface normal N such that a direction of drifting electrons and holes in the X-ray detector device 10 is on average different from a coupling direction C, which is a direction of incoming X-rays or more precise, a direction parallel to an axis of symmetry of a beam of X-ray radiation.

The adjacent cathode pixels 111 and the adjacent anode pixels 121 are put at a constant high voltage offset with respect to one another in order to avoid a charge being carried away in a direction N perpendicular to the cathode surface 11 or the anode surface 12. Such a voltage offset $\Delta U$ can be tuned to have a suitable polarity to converge a charge transport direction T to the coupling direction C. By aligning the charge transport T parallel to the coupling direction C, an approach of the charge transport direction T to the coupling direction C is to be understood. Once implemented, charge can travel parallel to the coupling direction C onto the anode pixels 121 and a degradation of lateral spectral resolution is reduced or avoided.

The calibration can be made by a modulation transfer function (MTF) calibration method. The calibration can be made to maximize spatial resolution as a function of the voltage offset $\Delta U$ to achieve the best restoration.

According to the present invention, also a computer program element is presented, wherein the computer program element comprises program code means for causing an X-ray detector device 10 to carry out the steps of the X-ray imaging method when the computer program is run on a computer controlling the X-ray detector device 10.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A method for detection of X-ray radiation using an X-ray detector device at an inclined angle relative to the X-ray radiation, the method comprising:
providing an X-ray detector device including a cathode surface comprising cathode pixels, an anode surface comprising anode pixels, and a separation layer, wherein the cathode surface and the anode surface are displaced by the separation layer allowing charge transport between the cathode surface and the anode surface in response to the X-ray radiation incident during operation on the cathode surface, wherein the anode surface is segmented into the anode pixels, wherein the cathode surface is segmented into the cathode pixels, wherein at least one of the cathode pixels is assigned to at least one of the anode pixels in a coupling direction inclined relative to the cathode surface;
putting at least one of the cathode pixels at a voltage offset relative to an adjacent cathode pixel; and
putting at least one of the anode pixels at the voltage offset relative to an adjacent anode pixel, wherein the voltage offset is configured to converge charge transport in a direction parallel to the coupling direction, wherein the voltage offset depends on an inclination angle between the cathode surface and the coupling direction, and wherein the coupling direction is parallel to an axis of symmetry of a beam of the X-ray radiation incident during operation on the cathode surface.

2. The method according to claim 1, wherein the voltage offset is inversely proportional to an offset number x of cathode pixels between an arbitrary first cathode pixel and a second cathode pixel, wherein the second cathode pixel is defined to be on an equipotential line with an anode pixel aligned with the first cathode pixel in a direction normal to the cathode surface.

3. The method according to claim 1, wherein the voltage offset is inversely proportional to an offset number x of anode pixels between an arbitrary first anode pixel and a second anode pixel, wherein the second anode pixel is defined to be on an equipotential line with a cathode pixel aligned with the first anode pixel in a direction normal to the cathode surface.

4. The method according to claim 1, wherein the voltage offset is $$\Delta U = (U_C - U_A)\frac{p}{d}\tan\varphi,$$

wherein $U_C$ is a cathode voltage of a cathode pixel, wherein $U_A$ is an anode voltage of an anode pixel, wherein said cathode pixel and said anode pixel are aligned in a direction normal to the cathode surface, wherein p is an anode pitch, wherein d is a distance between the cathode surface and the anode surface, and wherein $\varphi$ is an angle between the coupling direction and a cathode surface normal.

5. The method according to claim 4, wherein the ratio p/d is between 0.5 and 7.

6. The method according to claim 1, wherein the inclination angle between the cathode surface and the coupling direction is between 5° and 89°.

7. The method according to claim 1, further comprising:
using an X-ray tube to generate the beam of the X-ray radiation incident during operation on the cathode surface of the X-ray detector device with an inclination angle between the axis of symmetry of the beam of the X-ray radiation and the cathode surface.

8. The method according to claim 7, further comprising processing interference fringes detected by the X-ray detector device for phase-contrast imaging.

9. The method according to claim 1 further comprising:
providing the X-ray radiation to radiate the cathode surface of the X-ray detector device with an inclination angle, and
detecting the X-ray radiation by the X-ray detector device.

10. The method according to the claim 9, further comprising:
measuring a resolution phantom for various values of the voltage offset, and
calibrating the X-ray detector device by maximizing a spatial resolution as a function of the voltage offset.

* * * * *